(12) United States Patent
Hartick et al.

(10) Patent No.: US 6,483,894 B2
(45) Date of Patent: Nov. 19, 2002

(54) APPARATUS AND METHOD FOR ADJUSTING A COLLIMATOR

(75) Inventors: Martin Hartick, Bad Nauheim; Frank Cordes, Neustadt, both of (DE)

(73) Assignee: Heimann Systems GmbH, Wiesbaden (DE)

( * ) Notice: Subject to any disclaimer, the term of this patent is extended or adjusted under 35 U.S.C. 154(b) by 0 days.

(21) Appl. No.: 09/759,643

(22) Filed: Jan. 16, 2001

(65) Prior Publication Data

US 2001/0036250 A1 Nov. 1, 2001

Related U.S. Application Data

(63) Continuation of application No. 09/645,487, filed on Aug. 25, 2000.

(30) Foreign Application Priority Data

Nov. 13, 1999 (DE) .......................................... 199 54 661

(51) Int. Cl.[7] .................................................. G21K 1/02
(52) U.S. Cl. ......................... 378/147; 378/143; 378/16
(58) Field of Search ................................. 378/147, 145, 378/16; 250/515.1, 505.1

(56) References Cited

U.S. PATENT DOCUMENTS

| 4,203,037 A | | 5/1980 | Gur et al. |
| 5,787,145 A | | 7/1998 | Geus |
| 6,175,615 B1 | * | 1/2001 | Guru et al. ................. 378/149 |
| 6,298,117 B1 | * | 10/2001 | Hampel et al. ............. 378/150 |

FOREIGN PATENT DOCUMENTS

| DE | 35 26 015 A1 | 1/1987 |
| DE | 41 30 039 A1 | 3/1993 |
| DE | 41 37 242 A1 | 5/1993 |
| DE | 195 10 168 A1 | 9/1996 |
| JP | 5-215898 | 8/1993 |
| JP | 10-246797 | 9/1998 |

* cited by examiner

*Primary Examiner*—David P. Porta
*Assistant Examiner*—Pamela R. Hobden
(74) *Attorney, Agent, or Firm*—Birch, Stewart, Kolasch & Birch, LLP

(57) ABSTRACT

A collimator for an X-ray testing machine and a method for adjusting the collimator with the aid of a detection system disposed in the collimator that includes at least two spatially separate detection devices, disposed and spacing one behind the other.

13 Claims, 3 Drawing Sheets ic_ref id="N" />

APPARATUS AND METHOD FOR ADJUSTING A COLLIMATOR

CROSS-REFERENCE TO RELATED APPLICATIONS

This application is a continuation of U.S. application Ser. No. 09/645,487 filed Aug. 25, 2000.

This application is related to concurrently filed U.S. application Ser. NoS. 09/645,485, 09/645,486 and Ser. No. 09/645,484 and which are continuations of respective U.S. application Ser. Nos. 09/645,485, 09/645,486 and 09/645,484, each filed Aug. 25, 2000, the subject matter of each such application being incorporated herein by reference.

FIELD OF THE INVENTION

The invention relates to an apparatus and a method for adjusting a collimator, especially a collimator for an X-ray testing machine having an x-ray source and elements for generating a primary beam.

BACKGROUND OF THE INVENTION

Alignment and adjustment of a collimator and detector apparatus in an X-ray machine has a decisive impact on selectivity and, consequently, a decisive impact on material recognition and the probability of detecting an object. This is especially true in X-ray machines that employ X-ray diffraction, where an exact adjustment is critical for precisely measuring and determining the detected material based on the exact angular position of the collimator and detector apparatus relative to the X-ray beam.

German published Patent Application DE 195 10 168 A1 discloses an example of adjusting a collimator and detector apparatus in an X-ray testing machine. In this case, an automatic readjustment is performed prior to each measurement. The collimator and detector apparatus, which comprises a plurality of collimators with detectors respectively located behind them, is disposed on a carrier unit. The carrier unit includes an additional, central collimator that is oriented toward the focus of an X-ray-generating X-ray source, or is oriented with each readjustment. During an adjustment, the central beam (primary beam) emitted by the X-ray source and passing through the central collimator in an exact orientation, generates detection signals on adjacent individual detectors disposed behind the central collimator, with the signals being of identical magnitude when the adjustment is exact.

BRIEF SUMMARY OF THE INVENTION

It is an object of the invention to provide an apparatus and a method for the adjustment of a collimator in an X-ray testing machine that is structurally simpler than those previously known, and is completely automatic.

The above object generally is achieved according to a first aspect of the invention by an apparatus that includes a collimator for an X-ray testing machine having an X-ray source for generating X-ray radiation and elements for generating a primary beam, and wherein the collimator has a central, blind-bore-like opening and first and second detection devices, which are spatially separated disposed and spaced one behind the other inside the central opening, for orienting the collimator relative to the primary beam.

The above object generally is achieved according to a second aspect of the invention by a method for adjusting a collimator in an X-ray testing machine relative to a primary X-ray beam by using first and second X-ray detection devices, which are spatially separated, disposed and spaced one behind the other along the primary beam, to spatially orient the collimator so that the primary beam impacts the centers of the first and second detection devices at a right angle, the method comprising, in the first step, moving the collimator until a signal at the first detection device is maximal; in a second step, rotating the collimator in two independent planes about a point preferably located near the center of the first detection device until a signal from the second detection device is maximal. This is achieved by first rotating the collimator in plane one. An intensity maximum on the second detection device is obtained and subsequently rotating the collimator in plane two, which is independent of plane one until maximum is achieved on both detection devices.

The concept underlying the invention is to perform the adjustment with the aid of a detection system disposed in the collimator and comprising at least first and second spatially separated detection devices that are placed one behind the other. In the case of a homogeneous attenuation of a primary beam emitted by an X-ray source through the first detection device of the detection system, the remaining beam intensity is used once more for the final orientation of the collimator with the aid of the second detection device. In this way, it is possible to attain an exact, coaxial orientation of the collimator on or along the axis of the primary beam, thereby assuring a higher measuring precision within an X-ray machine. The further apart the first and second detection devices are spaced, the more precise the orientation of the collimator inside an X-ray machine will be.

For the spatially local orientation of the collimator in a first point, the first detection device is moved in the primary beam until a signal generated in the process is maximal, that is, the most intense. For an optimum orientation of the collimator along the primary beam, the orientation is then effected relative to a further point in the collimator. This is attained with the aid of the second detection device, with the collimator being rotated in a (higher) plane about an imaginary point (located as close as possible to the center of the first detection device) in two independent planes until the signal is also maximal in the second detection device, without minimizing the signal at the first detection device. After the maximum in the first rotational plane has been established in this manner, a further rotation takes place in the second rotational plane; here, too, the center of rotation lies as close as possible to the center of the first detection device. The optimum orientation is assured if the intensity maximum is established in both detection devices.

In a simple embodiment, a collimator arrangement comprising, for example, apertured diaphragms, can be mounted in front of each of the two detection devices in the collimator. These apertures or collimator adapt the respective detection surface to the beam diameter of the primary beam. When using detection devices whose sensitive surfaces coincide sufficiently with the beam diameter, the collimator arrangement can be omitted.

A semiconductor, gas or scintillation counter that is sufficiently thin and homogeneous can be used as the first detection device. Such a counter only effects a slight attenuation of the primary beam, and essentially retains the intensity distribution of the incident beam in the transmitted beam. A semiconductor, gas or scintillation counter can also be used as the second detection device. Its absorption properties must, however, be matched to the—on average, higher—energy of the quanta of the resulted beam transmitted through the first detection device.

The two spatially separated detection devices can each respectively comprise a four-quadrant detector, at least two individual detectors, a detector array or position-sensitive detector having multiple-segmented diodes.

The method is preferably used to adjust round-slot collimators with a detector, e.g. crystal detector, located behind them. In this case, the system is set at a predetermined angle relative to the primary beam for an exact measurement employing X-ray diffraction.

It is also possible to adjust a simple collimator/detection device that is used, for example, in conventional material detection. In this case, the first detection device is embodied as a detector for the relatively lower-energy component of the radiation, and the second detection device is embodied as a detector for the relatively higher-energy component.

The invention is described in detail below by way of an embodiment illustrated in the drawings.

DETAILED DESCRIPTION OF THE PREFERRED EMBODIMENTS

Figure 1:
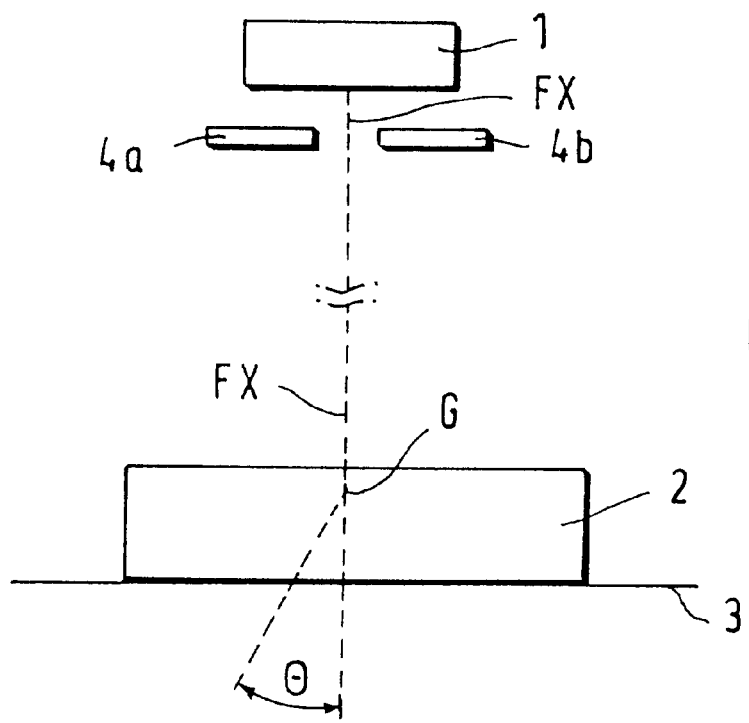
FIG. 1 is a schematic illustration of a basic representation of a measurement path according to the state of the technology.

FIG. 1 illustrates a measurement path in an X-ray (testing) machine, not shown in detail. In a known manner, an X-ray source 1 generates X-ray radiation FX and radiates it onto an object 2 to be X-rayed, the object 2 being located on a transport device 3. A collimator or aperture arrangement 4a, 4b generates a primary beam $FX_1$ preferably as a pencil beam.

As dictated by the crystal-lattice structure of the material of the object 2 to be X-rayed, the primary beam $FX_1$ is diffracted in a known way at a plurality of lattice points G (only one is shown here). As a result of the diffraction at the lattice points, at least part of the primary beam $FX_1$ is deflected as the radiation $FX_1'$ with a specific beam energy at an angle $\Theta_M$ that is a function of the material. In a known manner, this condition is utilized to determine the material in the beam on the basis of the physical effect of X-ray diffraction (Bragg's interference pattern). Through the predetermined of a specific angle $\Theta_M$, different energies are measured (in accordance with Bragg) and compared to known values.

Figure 2:
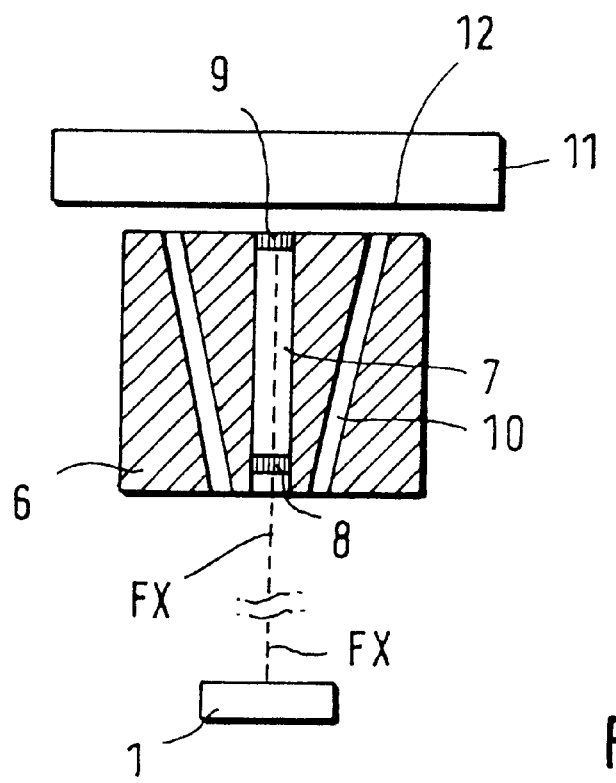
FIG. 2 is a schematic illustration of one embodiment of the invention with a round-slot collimator.

FIG. 2 illustrates a collimator 6, which can be used to determine the material or type of material of the object X-rayed with the primary beam $FX_1$ (FIG. 1). The collimator 6 is a round-slot collimator with a crystal detector 11 disposed behind it. Both the collimator 6 and the detector 11 are used for a measurement employing X-ray diffraction. A blind-bore-like opening 7 that is integrated into the center of the collimator 6 acts as a central collimator. At a radial distance from the central opening 7, the collimator 6 has a conically-expanding round slot 10, which determines an angular path of the predetermined angle $\Theta_M$. Disposed inside the opening 7 are a first detection device 8 and, behind it at a defined distance, a second detection device 9. The surface of the crystal detector 11 is large enough to permit the scattering-cone beams (radiation $FX_1'$) exiting through round slot 10 to be recorded. The crystal 11 has a preferably circular, X-ray-sensitive surface 12 that faces the collimator 6. The X-ray source is indicated by 1 in FIGS. 1–3.

Figure 3:
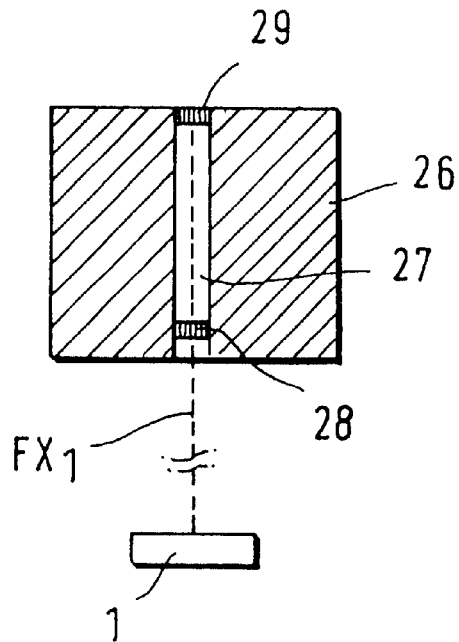
FIG. 3 is a schematic illustration of an embodiment of the invention using a simple collimator.

FIG. 3 depicts a further collimator 26, which has a first detection device 28 in a central, blind-bore-like opening 27, and a second detection device 29 at a defined distance from the first detection device, preferably at the rear end of the passage 27. The first detection device 28 is embodied as a detector for relatively lower X-ray energies, while the second detection device 29 is embodied as a detector for relatively higher X-ray energies. This collimator/detection device is used, for example, for conventional material detection.

Figure 4:
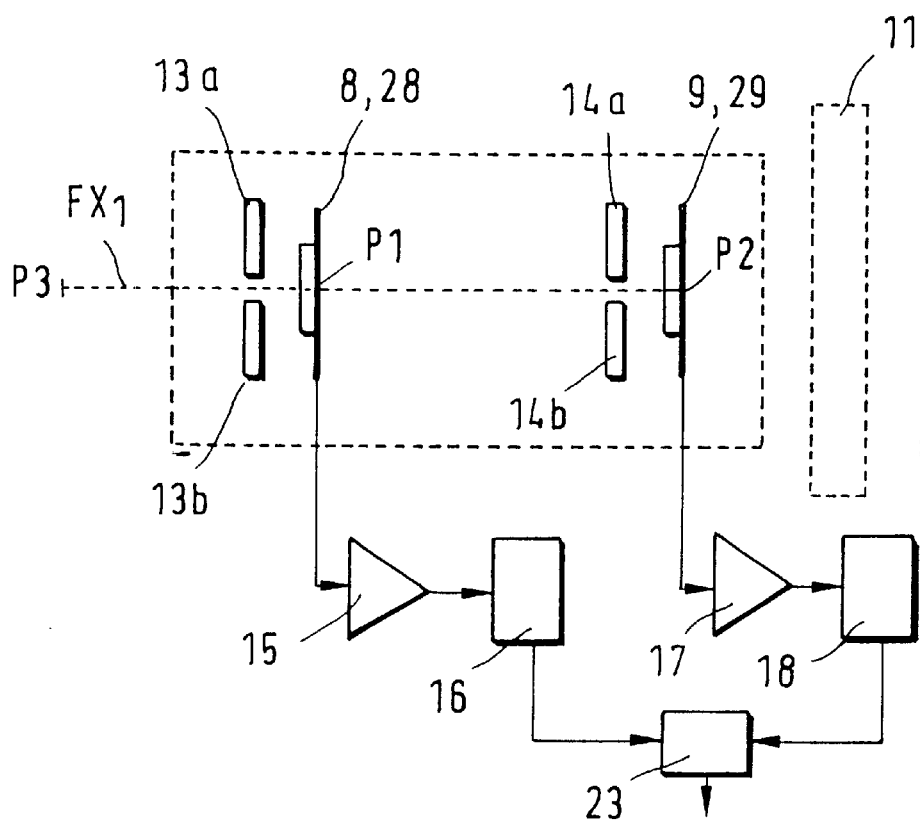
FIG. 4 shows an embodiment of the apparatus according to the invention.

FIG. 4 schematically shows the inside structure of the collimator 6, 26 with the electrical connections for signal evaluation, which are necessary for adjustment. Apertured-diaphragm arrangements 13a, 13b and 14a, 14b, are disposed, respectively, in front of the detection device 8, 28 or the detection device 9, 29. These arrangements adapt the detection surface of the detection device 8, 28 or the detection device 9, 29 to the diameter of the primary beam $FX_1$. Elements 15 and 17 represent signal-amplifier stages, which are necessary for amplifying the signals picked up at the respective detection devices 8, 28 and 9, 29. These amplifier stages 15 and 17 are connected to display units 16 and 18, respectively, and are also connected to a microprocessor (computer) 23. The additionally-illustrated crystal detector 11 is omitted if a simple collimator 26 is to be adjusted instead of a ring-slot collimator 6.

Figure 5:
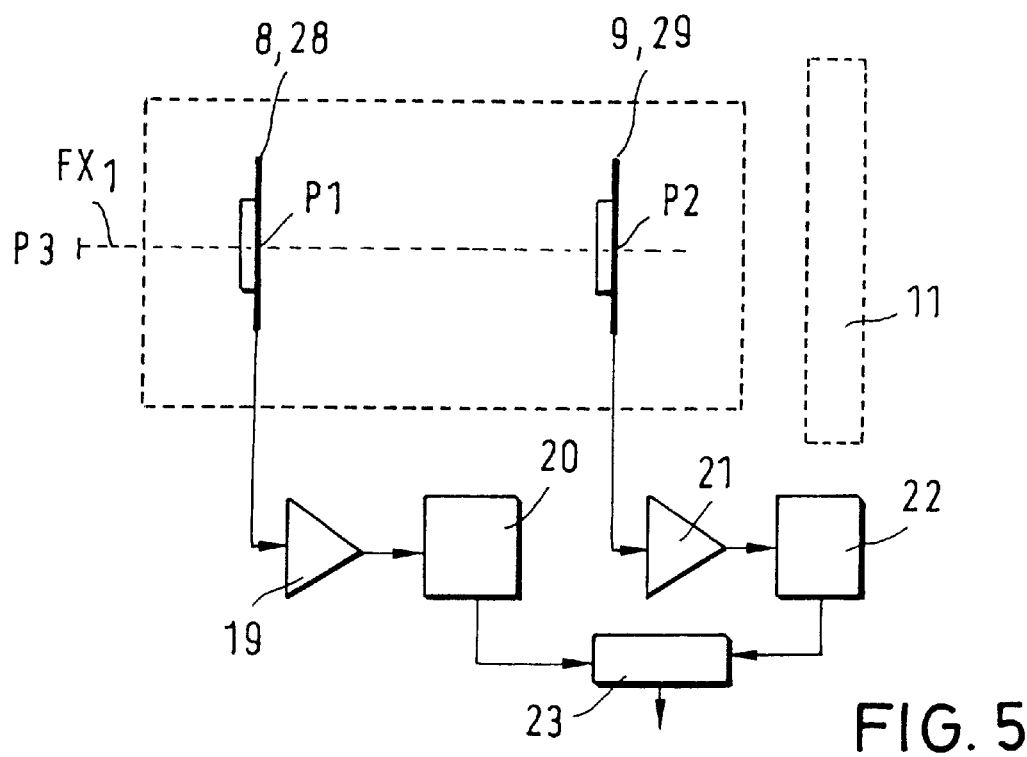
FIG. 5 shows a further embodiment of the apparatus of according to the invention.

A further embodiment according to FIG. 5 employs detection devices 8, 28, 9, 29, which permit the determination of the center of gravity of the intensity distribution of the X-ray or primary beam $FX_1$ impacting them. The detectors can be numerous individual detectors, detector arrays, four-quadrant detectors or position sensitive detectors having multiple-segmented diodes. Amplifier stages that operate in parallel are disposed downstream of these detection devices 8, 28, 9, 29; for the sake of a clear overview, the stages are only indicated by a respective reference numeral 19 or 21. An amplifier of the respective amplifier stage 19, 21 is associated with each individual detector, each detector in the array and each diode in the detection devices 8, 28, 9, 29. A display unit 20 or 22 is disposed downstream of these amplifier stages 19, 21. The amplifier stages 19, 21 are also electrically connected to the microprocessor 23. The first collimator arrangement 13a, 13b and the second collimator arrangement 14a, 14b, or only the second collimator arrangement 14a, 14b from FIG. 4, can be omitted if the orientation is effected in a pencil beam (point beam) $FX_1$.

Figure 6:
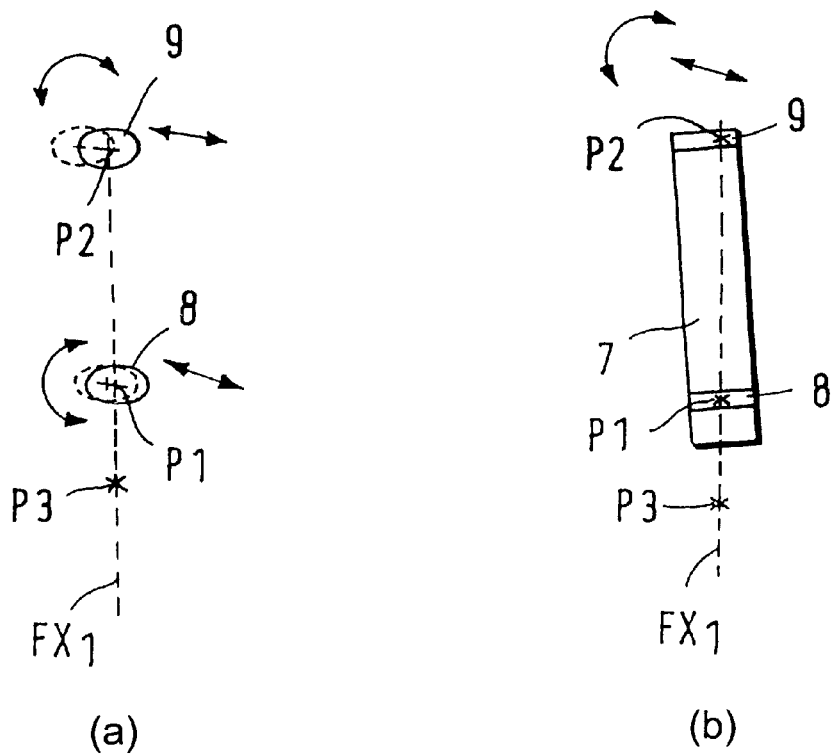
FIGS. 6a and 6b are schematic representations of the orientation of the collimator relative to a primary beam during the method according to the invention.

Regardless of the embodiment, the adjustment process is performed as follows:

As shown in FIG. 6, the X-ray radiation emitted as a primary beam $FX_1$ and observed inside the passage 7 prior to the adjustment may be located outside of the center of the first and second detection devices 8, 28 and 9, 29. A first point P1 that is predetermined for the adjustment and a second point P2 on the primary beam do not coincide with the respective center point (center) of the detection device 8, 28 or 9, 29. Consequently, the collimator 6, 26 must be oriented spatially, that is, in three planes, to reach its optimum spatial position without having any tilt relative to the primary beam $FX_1$.

In a first step of the adjustment, the collimator 6, 26 is moved, for example in a plane perpendicular or approximately perpendicular to the propagation direction of primary beam, until the generated signal is maximal in the first detection device 8, 28. The primary beam $FX_1$ lies in the point P2, further outside of the center of the second detection device 9, 29. The signals generated in the detection devices 8, 28 and 9, 29 are displayed on the display unit 16 and 20, respectively.

For the optimum orientation of the collimator 6, 26, it is necessary to orient the collimator toward the second point P2 in a second step. For the orientation toward this point, the collimator 6, 26 is rotated or adjusted in two independent planes about an imaginary point P3, which is preferably located near the center of the first detection device 8, 28, until the signal from the second detection device 9, 29 is also at its maximum. This rotational plane encompasses a pointed conical region (see arrows) originating from the point P3. After this second step, the maximum of the first rotational plane is established, effecting a first local pre-orientation of the collimator 6, 26.

After the intensity maximum in the first plane has been determined, the rotation in the second rotational plane is initiated for the further spatial orientation. A point near the center of the first detection device 8, 28 is also selected for this orientation; the point P3 can serve as a reference. Also in this case, the collimator 6, 26 is rotated inside the pointed conical region such that the intensity maximum is established at the respective detection devices 8, 28 or 9, 29. This procedure is also to be performed in the third rotational plane, so the primary beam $FX_1$ then impacts the centers of the first and second detection devices 8, 28, 9, 29 at a right angle.

The order of the collimator moving and rotating steps may be varied depending, for example, on the initial alignment condition and alignment reproducibility.

In an embodiment comprising a plurality of position-sensitive detectors, the amplitudes of the individual signals of the detection devices 8, 28 and 9, 29 are first analyzed step-wise in the microprocessor (computer) 23 and further processed. The current position of the beam center of the primary beam $FX_1$ is determined from the individual signals and compared to the center of the respective detection device 8, 28 or 9, 29. The detection centers are readjusted to the beam center of the primary beam $FX_1$ until the generated signal values are at their maximum. In this way, an offset between the respective detection center and the center of the primary beam can be more clearly identified and corrected in one step with the aid of a one-time calibration.

In an embodiment comprising a four-quadrant detector in the detection device 8, 28 or 9, 29, the signals generated quadrant-wise are evaluated, with the detection center being established when the primary beam $FX_1$ impacts the common intersection of the quadrants and generates signals of identical magnitude in each quadrant.

Thus, simplified means are used to effect an optimum orientation of the collimator 6, 26 along a primary beam $FX_1$. The collimator position in an X-ray testing machine (not shown in detail here) is sequentially varied with the aid of a regulating device (not shown in detail here) until both of the detection devices 8, 28 and 9, 29 are impacted maximally by the primary beam $FX_1$.

The collimator 6, 26 is rotated stepwise in the individual planes by mechanical elements installed in the X-ray machine, which are automatically controlled and regulated with a program controlled by the microprocessor (computer) 23. The intensity maxima determined in the first adjustment can be stored for future use.

In the use of a calibrated collimator 6, 26 with a plurality of location-sensitive detectors, a one-time measurement can immediately reveal the offset between the primary-beam maximum and the detection center, and the method can correct the offset.

It is further possible to use a plurality of detection devices that are disposed one behind the other inside the passage 7, but it is not necessary for the adjustment process itself, because this feature renders the method more costly.

The invention now being fully described, it will be apparent to one of ordinary skill in the art that many changes and modifications can be made thereto without departing from the spirit or scope of the invention as set forth herein.

What is claimed is:

1. An X-ray testing machine comprising:
    an X-ray source for generating X-ray radiation;
    elements for generating a primary beam of the x-ray radiation;
    a collimator for the x-ray radiation;
    means for orienting the collimator relative to the primary beam including a central, blind-bore opening in said collimator; and
    first and second detection devices disposed and spaced one behind the other inside the central opening.

2. The apparatus according to claim 1, wherein a collimator arrangement is mounted in front of the first detection device.

3. The apparatus according to claim 2, wherein a collimator arrangement is mounted in front of the second detection device.

4. The apparatus according to claim 1, wherein the collimator is a ring-slot collimator having a conically-expanding round slot that is spaced from the central opening, said slot determining an angular path of a predetermined angle.

5. The apparatus according to claim 4, wherein a detector is fixedly associated with the collimator and possesses an X-ray-sensitive surface that faces the collimator, said detector being oriented such that scattering-cone beams exiting the slot are received by said detector.

6. The apparatus according to claim 1, wherein at least one of the first and second detection devices comprise a four-quadrant detector.

7. The apparatus according to claim 1, wherein at least one of the first and second detection devices comprise at least two individual detectors.

8. The apparatus according to claim 1, wherein at least one of the first and second detection devices are constructed from position-sensitive detectors having multiple-segmented diodes.

9. The apparatus according to claim 1, wherein at least one of the first and second detection devices comprise a detector array.

10. The apparatus according to claim 1, wherein the first detection device, which is disposed closer to the x-ray source, detects relatively lower energy X-rays, and the second detection device detects relatively higher energy X-rays.

11. The apparatus according to claim 1, further comprising a first amplifier stage electrically connected to the first detection device; a second amplifier stage electrically connected to the second detection device; and a central microprocessor connected downstream of the first and second amplifier stages.

12. A method for adjusting a collimator in an X-ray testing machine relative to a primary X-ray beam comprising: providing first and second X-ray detection devices, which are spatially separated, disposed and spaced one behind the other along the primary beam; and, using the signal from the first and second detection devices to spatially orient the collimator so that the primary beam impacts the centers of the first and second detection devices at a right angle by:

in a first step, moving the collimator until a signal at the first detection device is maximal; and in a second step, rotating the collimator in two independent planes about a point in a first rotational plane until a signal from the second detection device is maximal.

13. The method according to claim 12, further comprising using a microprocessor to evaluate the signals from the first and second detection devices and to determine the position of the intensity maximum in the rotation plane, with the individual signals being evaluated to directly determine the offset between a primary-beam center and detection centers of the first and second detection devices, which must then be readjusted.

* * * * *